(12) United States Patent
Brockmann et al.

(10) Patent No.: US 12,251,157 B2
(45) Date of Patent: Mar. 18, 2025

(54) ELECTRODE INSTRUMENT AND RESECTOSCOPE WITH GRIPPING FUNCTION

(71) Applicant: OLYMPUS WINTER & IBE GMBH, Hamburg (DE)

(72) Inventors: Christian Brockmann, Hollenstedt (DE); Hannes Miersch, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 85 days.

(21) Appl. No.: 16/811,675

(22) Filed: Mar. 6, 2020

(65) Prior Publication Data

US 2020/0289189 A1    Sep. 17, 2020

(30) Foreign Application Priority Data

Mar. 13, 2019  (DE) .......................... 102019106430.9

(51) Int. Cl.
*A61B 18/14* (2006.01)
*A61B 18/00* (2006.01)
*A61B 18/12* (2006.01)

(52) U.S. Cl.
CPC .. *A61B 18/149* (2013.01); *A61B 2018/00083* (2013.01); *A61B 2018/00517* (2013.01); *A61B 2018/00601* (2013.01); *A61B 2018/126* (2013.01); *A61B 2018/1407* (2013.01)

(58) Field of Classification Search
CPC ........ A61B 18/149; A61B 2018/00083; A61B 2018/00517; A61B 2018/00601; A61B 2018/126; A61B 2018/1407
See application file for complete search history.

(56) References Cited

U.S. PATENT DOCUMENTS

| 5,196,011 A | 3/1993 | Korth et al. |
| 5,408,992 A * | 4/1995 | Hamlin ................ A61B 5/0088 600/109 |
| 5,423,813 A | 6/1995 | Kaiser et al. |

(Continued)

FOREIGN PATENT DOCUMENTS

| DE | 10122465 C1 | 8/2002 |
| DE | 102006053338 A1 | 5/2008 |

(Continued)

OTHER PUBLICATIONS

Sep. 17, 2021 Office Action Issued In U.S. Appl. No. 16/775,496.

(Continued)

*Primary Examiner* — Eun Hwa Kim
*Assistant Examiner* — Catherine C. Premraj
(74) *Attorney, Agent, or Firm* — Oliff PLC (57) ABSTRACT

An electrode instrument for use in a resectoscope, the electrode instrument having an elongate shaft portion with two support arms through which a conductor extends that forms an electrode at the distal end of the electrode instrument that can be subjected to high-frequency current and is arranged between the distal ends of the support arms, wherein at least one of the support arms has in its distal end region a tissue contact part for holding tissue fragments that is arranged on the outer wall of the support arm and angled in relation to the longitudinal axis of the support arm; and to a corresponding resectoscope.

11 Claims, 4 Drawing Sheets

(56) References Cited

U.S. PATENT DOCUMENTS

| | | |
|---|---|---|
| 6,068,603 A | 5/2000 | Suzuki |
| 6,149,620 A | 11/2000 | Baker et al. |
| 7,150,745 B2 | 12/2006 | Stern et al. |
| 7,261,711 B2 | 8/2007 | Mulier et al. |
| 7,303,561 B2 | 12/2007 | Ouchi |
| 7,347,860 B2 | 3/2008 | Ouchi |
| 7,572,251 B1 | 8/2009 | Davison et al. |
| 7,815,639 B2 | 10/2010 | Brommersma |
| 9,072,443 B2 | 7/2015 | Hashido et al. |
| 2002/0111608 A1 | 8/2002 | Baerveldt et al. |
| 2002/0188293 A1 | 12/2002 | Manzo |
| 2002/0193792 A1 | 12/2002 | Valencic et al. |
| 2003/0144605 A1 | 7/2003 | Burbank et al. |
| 2003/0187324 A1 | 10/2003 | Gatto |
| 2004/0044343 A1 | 3/2004 | Brommersma et al. |
| 2005/0080412 A1 | 4/2005 | Ouchi |
| 2006/0030644 A1 | 2/2006 | Hairston et al. |
| 2006/0069303 A1 | 3/2006 | Couvillon |
| 2007/0093812 A1* | 4/2007 | Hayashida ............ A61B 18/149 606/46 |
| 2009/0043303 A1 | 2/2009 | Shimomura |
| 2009/0270859 A1 | 10/2009 | Hirvi |
| 2012/0095458 A1 | 4/2012 | Cybulski et al. |
| 2012/0197245 A1 | 8/2012 | Burnett et al. |
| 2013/0218243 A1 | 8/2013 | Schomacker et al. |
| 2013/0226165 A1 | 8/2013 | Manwaring et al. |
| 2014/0171824 A1 | 6/2014 | Hugle et al. |
| 2014/0236143 A1* | 8/2014 | Ward ................ A61B 18/1442 606/39 |
| 2014/0379055 A1 | 12/2014 | Schomacker et al. |
| 2015/0005799 A1 | 1/2015 | Lindquist et al. |
| 2015/0011993 A1 | 1/2015 | Horlle |
| 2015/0327753 A1 | 11/2015 | Amirana et al. |
| 2015/0351826 A1 | 12/2015 | Kroeber et al. |
| 2016/0038028 A1 | 2/2016 | Buelna et al. |
| 2016/0120599 A1 | 5/2016 | Amirana et al. |
| 2016/0192983 A1 | 7/2016 | Klink et al. |
| 2016/0317213 A1* | 11/2016 | Wolter ................ A61B 18/149 |
| 2017/0014202 A1 | 1/2017 | Ransbury et al. |
| 2017/0071664 A1 | 3/2017 | Lim |
| 2019/0038341 A1 | 2/2019 | Brockmann et al. |
| 2020/0121791 A1 | 4/2020 | Zamadar |

FOREIGN PATENT DOCUMENTS

| | | |
|---|---|---|
| DE | 102013001156 A1 | 7/2014 |
| DE | 102017117749 A1 | 2/2019 |
| EP | 1 221 903 B1 | 6/2006 |
| EP | 1 974 683 A1 | 10/2008 |
| EP | 3 437 581 A1 | 2/2019 |
| WO | 2017/161331 A1 | 9/2017 |

OTHER PUBLICATIONS

Gerhard Lanzer. "Grundzüge Des Eisenstoffwechsels [Fundamentals of Iron Metabolism]". Klinik, 2010, vol. 6, pp. 43-46.

The U.S. Appl. No. 16/775,496, filed Jan. 29, 2020 in the name of Christoph Knopf.

The U.S. Appl. No. 16/775,572, filed Jan. 29, 2020 in the name of Christoph Knopf.

The U.S. Appl. No. 16/775,723, filed Jan. 29, 2020 in the name of Christian Brockmann et al.

Jun. 24, 2022 Office Action issued in U.S. Appl. No. 16/775,723.

Jul. 13, 2022 Office Action issued in U.S. Appl. No. 16/775,572.

Dec. 1, 2022 Office Action issued in U.S. Appl. No. 16/775,723.

Apr. 11, 2023 Office Action issued in U.S. Appl. No. 16/775,723.

Apr. 8, 2022 Final Office Action Issued in U.S. Appl. No. 16/775,496.

* cited by examiner

ELECTRODE INSTRUMENT AND RESECTOSCOPE WITH GRIPPING FUNCTION

BACKGROUND

The invention relates to electrode instruments for use in a resectoscope of the type cited in the preamble of claim 1 and to a resectoscope of the type cited in the preamble of claim 10.

Electrode instruments and resectoscopes of this generic type are used above all in urology for electrosurgical work in the bladder and urethra. They are usually used for resection and vaporization of tissue, for example tissue in the lower urinary tract. For this purpose, the resectoscopes comprise an electrode instrument that is supported in a longitudinally displaceable manner within the resectoscope shaft and, after insertion of the resectoscope, can be pushed with its distal working end out of the distal end of the shaft. The electrode instrument comprises an electrosurgical electrode at its distal working end, for example in the form of a loop or vaporization button (e.g., PlasmaButtons). Examples of such instruments include the OES PRO resectoscopes (Olympus) or other continuous-irrigation resectoscopes per Iglesias.

If the electrode instruments are used for resection of tissue, it is often desirable or necessary to remove the separated tissue from the site of the intervention, for example in order to prevent further spreading of a disease, such as in the case of a tumoral disease, and/or in order to take a tissue sample for diagnostic purposes. At present, tissue removal is often not performed by means of the resectoscope but rather using a separately inserted gripping instrument. However, this procedure entails the risks of tissue fragments being lost if the instruments are introduced successively or of different insertion openings having to be employed when the instruments are introduced at the same time, so that the intervention is less gentle on the patient. For this reason, it is desirable to be able to use the same instrument for resection and tissue extraction.

Existing resectoscopes have been used at times both for tissue resection and for tissue removal. After the electrosurgical separation of a tissue fragment from the surrounding tissue, for example by means of a loop electrode, the tissue fragment is clamped between the loop electrode and the inner tube that is arranged in the resectoscope shaft or the optics. The electrode instrument, tissue fragment, and inner tube were then pulled together from the outer shaft (cladding tube) of the resectoscope and thus also from the patient. However, this approach entails the risk of damaging the sensitive electrode. In addition, this gripping function depends on the geometry and arrangement of the electrode and inner tube, so that structural changes to these elements can lead to a loss or a change in the gripping function.

There is therefore a need for improved electrode instruments and corresponding resectoscopes for electrosurgical surgery by means of which tissues can both be severed and removed from the body.

DESCRIPTION

This object is achieved by an electrode instrument with the features of claim 1 and by a resectoscope with the features of claim 10. According to the invention, a provision is made in particular that a tissue contact part is arranged on at least one of the support arms of the electrode instrument between which and the distal end of the inner tube and/or a pass-through instrument tissue fragments can be clamped or on which tissue fragments can be impaled. The tissue fragments that are held in this manner on the electrode instrument or the resectoscope can then be removed from the patient's body.

In a first aspect, the invention therefore relates to an electrode instrument for use in a resectoscope, wherein the electrode instrument having an elongate shaft portion with two support arms through which a conductor extends that forms an electrode at the distal end of the electrode instrument that can be subjected to high-frequency current and is arranged between the distal ends of the support arms, characterized in that at least one of the support arms has in its distal end region a tissue contact part for holding tissue fragments that is arranged on the outer wall of the support arm and angled in relation to the longitudinal axis of the support arm.

In a second aspect, the invention relates to a resectoscope for endoscopic surgery with a cladding tube, characterized in that an electrode instrument according to the invention is supported so as to be longitudinally displaceable within the cladding tube. The resectoscope according to the invention is suitable for various interventions in endoscopic surgery, particularly in electrosurgical surgery. For instance, the resectoscope can be used for prostate resection. At the same time, the resectoscope can also be used for a variety of other operations, such as bladder resections.

In the standard embodiment, the resectoscope according to the invention has a tubular shaft. The resectoscope shaft comprises an elongate cladding tube. In addition to the shaft, the resectoscope for holding and operating comprises a handle system, which usually consists of two handle parts.

The electrode instrument according to the invention is used as a pass-through instrument in such a resectoscope. For this purpose, the electrode instrument is supported in a longitudinally displaceable manner in the resectoscope, preferably within the cladding tube of the resectoscope. The electrode instrument can be arranged outside an inner tube extending in the cladding tube, i.e., between the cladding tube and the inner tube, or inside the inner tube. In addition to the electrode instrument, further pass-through instruments can be arranged in the shaft of the resectoscope. The resectoscope usually additionally comprises rod-shaped optics, an illuminating means, and/or an irrigation system, for example.

In a conventional embodiment, the electrode instrument has an elongate shaft portion which, as described above, is arranged so as to be longitudinally displaceable and, optionally, rotatable about the longitudinal axis in the interior of the resectoscope shaft. The proximal end of the shaft portion is functionally connected to a carriage of the resectoscope transporter that can be actuated by means of the handle. An electrode that can be subjected to high-frequency current is formed at the distal end of the electrode instrument.

The electrode instrument has two support arms, particularly in the shaft portion. The electrode can be held securely between the distal ends of the two support arms without substantially impairing the view of the site of intervention. The support arms can extend from the distal end substantially straight to the proximal end of the electrode instrument. Alternatively, the support arms can be embodied as fork tubes and brought together in a fork proximally to the electrode. This arrangement has been found to be particularly space-saving and stable in some resectoscopes. Those skilled in the art are familiar with other suitable designs of the shaft portion. For example, it is also possible to have the support arms proximal to the electrode merge into a tubular electrode shaft. It is thus possible for the electrode instrument to also be used as an inner tube. According to the invention, it is therefore only necessary for the electrode instrument to have two support arms in its distal end region between which the electrode can be held.

A conductor extends through the support arms or the shaft portion and forms an electrode at the distal end of the electrode instrument to which high-frequency current can be applied. This conductor is electrically conductive and can be a conductor wire, for example. The conductor is electrically insulated from the resectoscope shaft, for example, toward the outside in the vicinity of the support arms. The support arms generally comprise an insulating sleeve—i.e., an electrically insulating sleeve—that encloses the conductor for this purpose. The insulating sleeve can have a hollow cylindrical shape in the interior of which the conductor extends. At the proximal end of the support arms, the conductor is connected to a power source via the proximal portion of the resectoscope.

The electrode formed by the conductor can have different shapes, but it is always supported between the distal ends of the two support arms. The electrode can be a loop electrode or a vaporization button, for example, the former being preferred.

According to the invention, at least one of the support arms has in its distal end region a tissue contact part for holding tissue fragments that is arranged on the outer wall of the support arm and angled relative to the longitudinal axis of the support arm. The tissue contact part that is arranged on a support arm enables tissue fragments to be held securely without having to burden the terminal electrode, so that the tissue fragments can be removed from the site of intervention in a safe and simple manner. The tissue fragments held are generally pulled out of the cladding tube of the resectoscope together with an inner shaft and/or the electrode instrument, so that the tissue fragments preferably have a maximum diameter that is smaller than the inside diameter of the cladding tube. However, it is also conceivable for the resectoscope to be removed completely from the site of the intervention along with a held tissue fragment in order to enable larger tissue fragments to also be removed from a patient's body.

The tissue contact part according to the invention is designed and arranged in such a way as to hold tissue fragments, preferably to hold tissue fragments between the tissue contact part and the distal end of an inner tube and/or the distal end of a pass-through instrument of a resectoscope. In these embodiments, the tissue fragment is thus clamped between the tissue contact part and a component of the resectoscope that is arranged proximally from the tissue contact part. In order to achieve this, the electrode instrument is first displaced distally in such a way that the tissue contact part is arranged distally from a severed tissue fragment, and then withdrawn in the proximal direction into the resectoscope shaft in such a way that the tissue fragment is clamped between the proximal surface of the tissue contact part and one of the abovementioned additional components of the resectoscope, preferably the distal end of an inner tube and/or a pass-through instrument, such as an optical system. It is sufficient for the tissue fragment to be supported on one side of the inner tube. It is not necessary for the tissue fragment to completely close the distal end of the inner tube.

Alternatively or in addition, the tissue contact part can be designed and arranged for piercing into tissue fragments. In this embodiment, it is not absolutely necessary for the proximal end of the fragment to be supported on an additional component of the resectoscope in order to hold the tissue fragment. Instead, the tissue contact part is long enough to securely hold a skewered tissue fragment. The tissue contact part designed to pierce tissue fragments is preferably flat in at least one dimension in order to enable the tissue fragment to be easily transfixed. The tissue contact part that is designed for piercing is preferably rod-shaped. As will be explained in greater detail below, the rod-shaped or otherwise-shaped tissue contact part can be bent or curved in order to be adapted to the dimensions of the resectoscope shaft.

It is also conceivable for the tissue contact part to have a tip that tapers to a point. This ensures that a tissue fragment can be quickly and securely pierced, picked up, and pushed onto the tissue contact part without falling apart during these steps.

According to the invention, at least one of the support arms has such a tissue contact part. It is conceivable for tissue contact parts to be arranged on both support arms. This is not necessary according to the invention, however. It may be advantageous for a tissue contact part to be arranged on only one of the support arms. Material and space can be saved in this way, for example.

The tissue contact part is arranged in the distal end region of the support arm. The tissue contact part should be arranged in a resectoscope distal from the distal end of the inner tube and/or pass-through instrument. This ensures not only that they are available as clamping partners, but also that there is sufficient space for the tissue fragment inside the cladding tube. When the electrode instrument displaced proximally as far as it will go, the tissue contact part can be arranged in the resectoscope, for example in the vicinity of the insulating tip of the resectoscope. Resectoscopes usually have such an electrically insulating tip at their distal end in order to prevent short circuits between the electrode and the electrically conductive components of the resectoscope.

The tissue contact part can be arranged in a portion of the support arm that is encased by an electrically insulating sleeve. The tissue contact part can also be made of an electrically insulating material. This is particularly advantageous, since there is no need to maintain an insulating gap between the tissue contact part and the electrode. Suitable electrically insulating materials are known to those skilled in the art and include ceramics and plastics, for example, particularly thermostable plastics. Alternatively, the tissue contact part can be arranged in a portion of the support arm that is not encased by an electrically insulating sleeve. The tissue contact part could then be arranged directly on the conductor, for example. In this embodiment as well, the tissue contact part can also be made of an electrically insulating material.

The tissue contact part is arranged on the outer wall of the support arm and angled relative to the longitudinal axis of the support arm. For example, the longitudinal axis of the tissue contact part can extend transverse or substantially transverse to the longitudinal axis of the support arm. However, the longitudinal axis of the tissue contact part preferably forms at least an angle of 140° to 40°, more preferably an angle of 120° to 60°, e.g., approximately 90°, relative to the longitudinal axis of the support arm. It will readily be understood that the tissue contact part does not have to form this angle along its entire length. Instead, the longitudinal axis of the tissue contact part forms said angles to the longitudinal axis of the support arm at least in some portions, it being preferred if at least one portion that is directly connected to the support arm forms said angle.

As already indicated above, the shape of the tissue contact part can be adapted to an inner shape of the resectoscope, meaning that it can be partially complementary to the shape of the resectoscope, e.g., to the inner wall of the cladding tube or inner tube. For example, starting from the support arm, the tissue contact part can extend away from the support arm in a partially circular shape. The curvature of the tissue contact part can correspond to the curvature of a loop electrode, for example. In the case of tissue contact parts that are curved in this way, it is preferred that the tissue contact part not be arranged directly proximally from (or, as seen from distal: behind) the loop electrode, but rather that it be arranged on the side of the support arm that faces away from the side into which the loop of the loop electrode extends.

According to the invention, the tissue contact part that is designed for piercing has a length and the tissue contact part that is designed for clamping has a proximal surface that is long or large enough to hold the tissue fragment securely. In particular, the tissue contact part should not slide off the tissue contact part when the inner tube and/or electrode instrument is pulled out of the cladding tube. In order to prevent slippage from the tissue contact part that is designed for piercing, the tissue contact part has, for example, a length that is at least ⅛ of the length of the electrode of the instrument, preferably at least ¼, more preferably at least ½. Starting from the support arm, the tissue contact part can extend at least into a sagittal plane of the electrode instrument that extends from the support arm to ⅛ of the distance to the second support arm, preferably ¼ of the distance. Sagittal planes are all planes that extend through the electrode instrument from top to bottom and proximal to distal; the terms "top" and "bottom" refer to a position of the instrument in which it is normally used and in which the handle of the resectoscope points downward, for example. The sagittal plane in the middle between the two support arms—i.e., the sagittal plane that extends from the support arm to ½ of the distance to the second support arm—can also be referred to as the median plane.

In order to render the holding of the tissue fragment between the tissue contact part and an additional component particularly secure, the tissue contact part can be arranged at least in some portions distally from an inner tube that is arranged in the cladding tube and/or from a pass-through instrument that is arranged in the cladding tube. In this context, the term "distal" denotes an arrangement in which the tissue contact part is arranged in a straight, axial extension of the corresponding component.

BRIEF DESCRIPTION OF THE FIGURES

Exemplary embodiments of the invention are shown schematically in the drawings. In the drawing.

EXEMPLARY EMBODIMENTS

Additional advantages, characteristics, and features of the present invention will become clear from the following detailed description of exemplary embodiments with reference to the attached drawings. However, the invention is not restricted to these exemplary embodiments.

Figure 1:
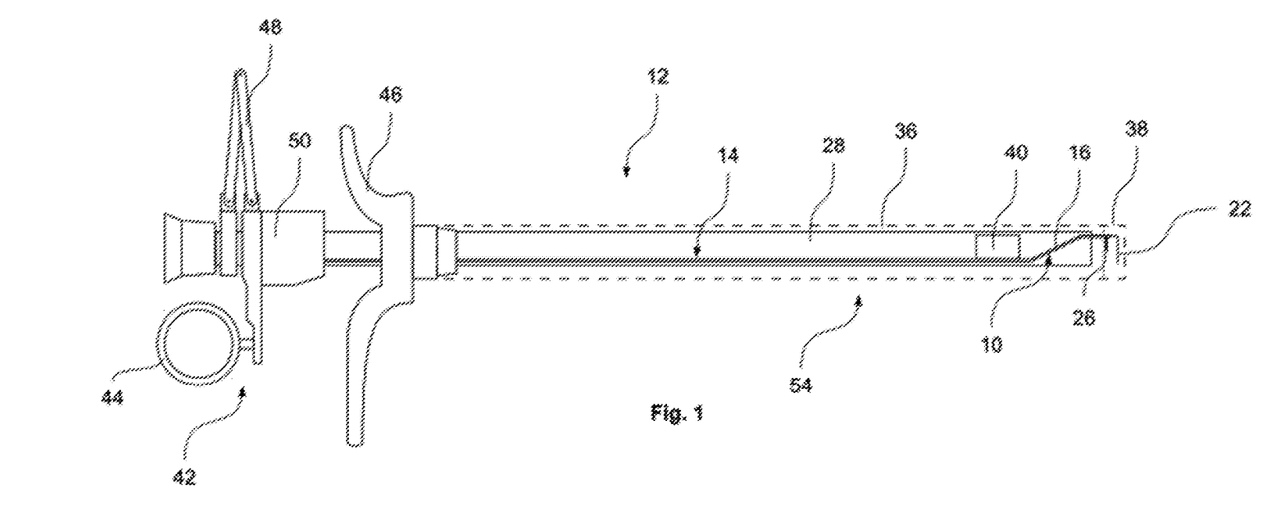
FIG. 1 shows a schematic sectional side view of a resectoscope according to the invention.
Figure 2:
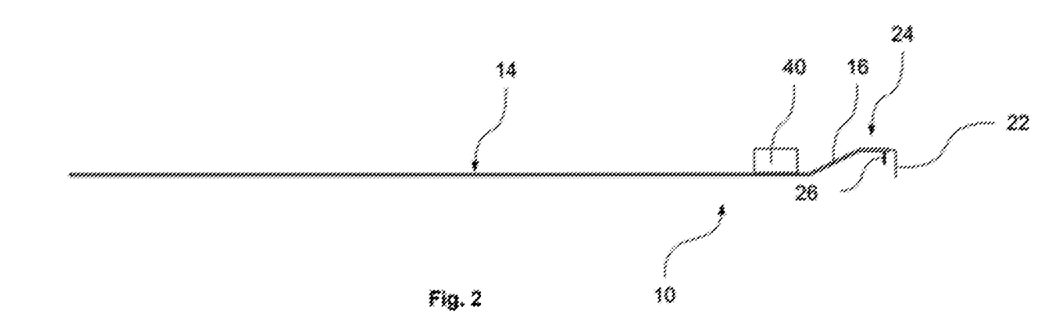
FIG. 2 shows a schematic sectional side view of an electrode instrument according to the invention.

FIG. 1 shows a sectional representation of a resectoscope 12 according to the invention, which comprises an electrode instrument 10 according to the invention. FIG. 2 shows the electrode instrument 10 separately from the resectoscope 12. In the standard design, the resectoscope 12 comprises a handle 42 and a shaft 54 that has an insulating tip 38 at its distal end. The handle 42 is designed to enable the resectoscope 12 to be held in one hand and for the pass-through instruments running through the shaft 54 to be actuated, preferably with one hand.

The resectoscope 12 shown has a passive transporter in which the slide 50 is displaced in the distal direction against the distal, first handle part 46 through a relative movement of the handle parts 44 and 46 that are arranged proximally from the shaft 54 against a spring force that is applied by a spring bridge 48. When the slide 50 is displaced in the distal direction against the handle part 46, the electrode instrument 10 is positively guided to the distal in a manner not shown. When the handle parts 44, 46 are released, the spring force generated by the spring bridge 48 forces the slide 50 back into its resting position, the electrode instrument 10 being pulled in the proximal direction. When the slide 50 is moved back, an electrosurgical intervention with the electrode instrument 10 can be carried out without manual force on the part of the surgeon—that is, passively.

The shaft 54 of the resectoscope 12 comprises a cladding tube 36 in whose interior a plurality of elongate pass-through instruments extend, particularly optics (not shown here) and the electrode instrument 10. The optics and additional pass-through instruments can extend in the inner tube 28, which is arranged in the cladding tube 36 between the support arms 16, 18 of the electrode instrument 10. For stability in its shaft portion 14, the electrode instrument 10 is secured by a holding element 40 against radial displacement. The holding element 40 has a partially circular cross section which, in the present instrument, bears against the outer wall of the inner tube 28. It is also conceivable for a holding element 40 to be supported on other elements of the shaft 54, for example on the inner wall of the cladding tube 36. The cross section of the holding element 40 is approximately semicircular in the present case, so that the holding element 40 positively engages against the outer wall of the inner tube 28 and the electrode instrument 10 can still be axially displaced. In other words, the holding element 40 has a shape that is partially complementary to the outer wall of the inner tube 28.

At its distal end, the electrode instrument 10 has an electrode 22 which, in the present case, is embodied as a loop electrode or cutting loop. The instrument is embodied as a bipolar instrument and is provided with a counterelectrode (not shown). The medical staff is able to remove tissue from the site of the intervention during a surgical intervention by means of the loop electrode.

In addition, the electrode instrument has a tissue contact part 26 on a support arm 16. The tissue contact part 26 is arranged in the distal end region 24 of the support arm 16. The electrode 22 is held in a distally spaced-apart manner at the distal end of the support arm 16. In the embodiment shown, the tissue contact part 26 extends radially inward from the support arm 16, i.e., toward the center of the cladding tube 36.

Figure 3:
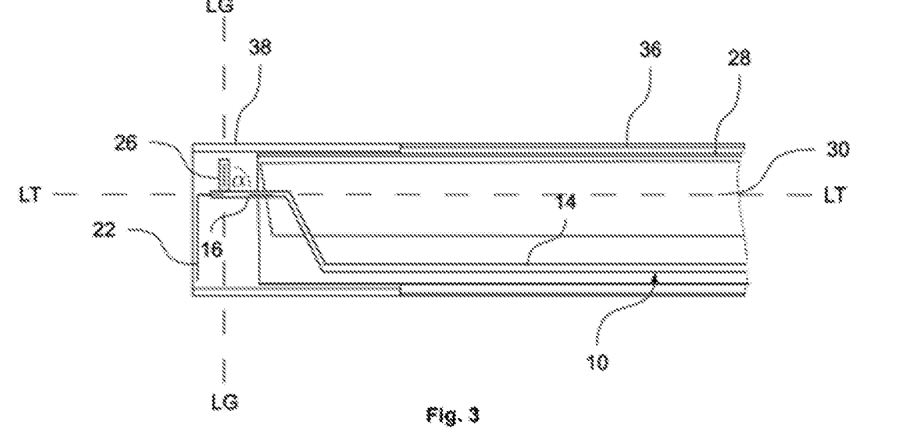
FIG. 3 shows a schematic sectional side view of the distal end region of a resectoscope according to the invention.

FIG. 3 shows a more detailed schematic sectional side view of the distal end region of an embodiment of the resectoscope 12 according to the invention. The electrode instrument 10 has a tissue contact part 26 which, starting from the support arm 16, extends in a manner contrary to that shown in FIGS. 1 and 2. The tissue contact part 26, particularly the longitudinal axis LG thereof, forms an angle α of 90° relative to the support arm 16, particularly to the longitudinal axis LT thereof. For the sake of clarity, the support arm 16 is shown thinner here than in the following figures. In the position shown, the electrode instrument 10 has been displaced as far as it will go proximally and is thus completely retracted into the cladding tube 36. In this position, both the electrode 22 and the tissue contact part 26 are arranged in the vicinity of the shaft 54 in which the insulating tip 38 forms the distal end of the shaft 54. At the same time, the tissue contact part 26 is arranged distally from the distal end of the inner tube 28 and pass-through instrument 30, which is a rod-shaped lens here.

Figure 4:
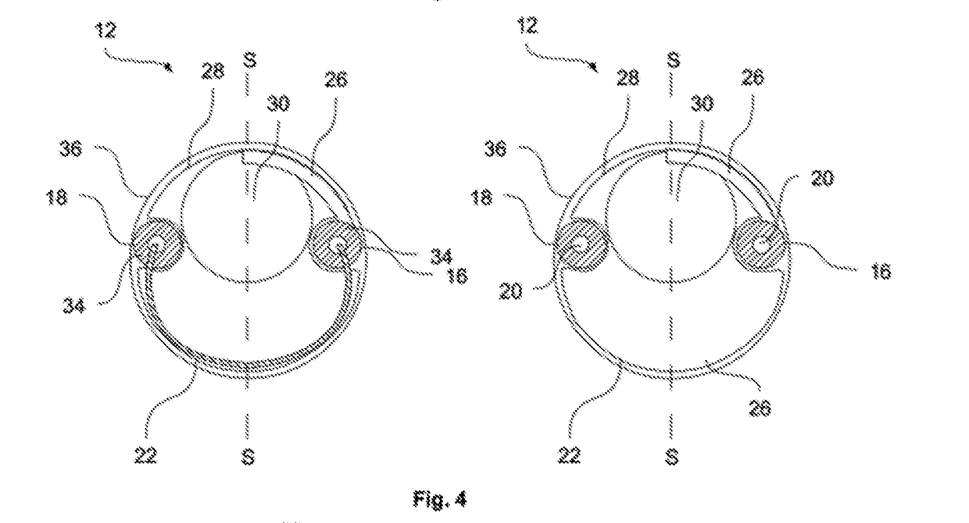
FIG. 4 shows a schematic frontal view of the end region shown in FIG. 3 (left) and a schematic sectional view along the axis "LG" in FIG. 3 (right)

As can also be seen particularly in FIG. 4, the tissue contact part 26 has the shape of a curved rod and is therefore suitable for piercing into a tissue fragment. FIG. 4 shows a schematic frontal view of the end region shown in FIG. 3 (left) and a schematic sectional view along the axis "LG" in FIG. 3 (right). The support arms 16 and 18 pass through the shaft of the resectoscope 12 between the cladding tube 36 and the inner tube 28. A pass-through instrument 30 (e.g., a lens) is arranged in the interior of the inner tube 28. An electrode 22 in the form of a loop is formed between the support arms 16, 18 at the distal end of the support arms 16, 18. Both support arms 16, 18 have an insulating sleeve 34 that is composed of an electrically insulating material. A conductor 20 in wire form is formed within the insulating sleeve 34 and forms the loop electrode at the distal end of the support arms 16, 18.

The tissue contact part 26 is arranged on the support arm 16 and is spaced proximally from the electrode 22 that is arranged on the support arm. The tissue contact part 26 extends from the support arm 16 approximately in the opposite direction relative to the direction in which the electrode 22 extends from the support arm 16. In this way, the arrangement of the tissue contact part 26 does not hinder the use of the electrode 22. The length of the tissue contact part 26 corresponds approximately to half the length of the electrode 22, the curvature of the two elements being approximately identical. The tissue contact part 26 is made to be somewhat thicker than the electrode 22.

Figure 5:
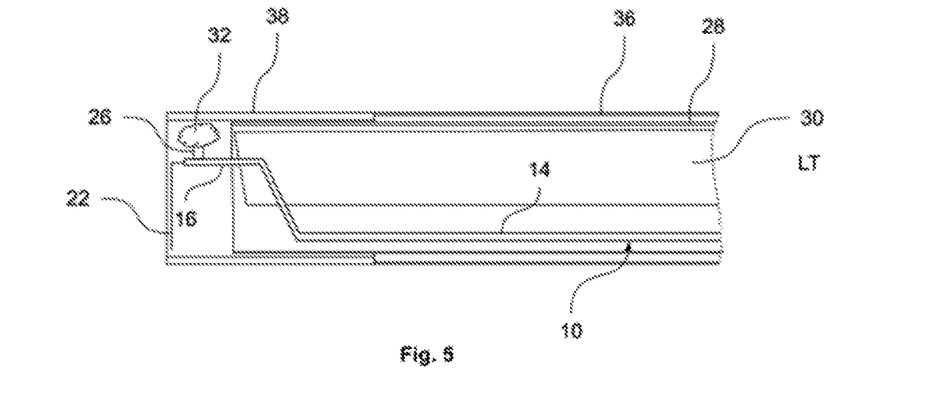
FIG. 5 shows a schematic sectional side view of the end region shown in FIG. 3, a tissue fragment being held on the tissue contact part.

FIG. 5 shows a schematic sectional side view of the end region shown in FIG. 3, a tissue fragment 32 being held on the tissue contact part. The tissue fragment 32 was first separated from the surrounding tissue of the patient by means of the electrode 22. The tissue contact part 26 was then impaled into the tissue fragment 32. Since the tissue fragment 32 has a size that at no point exceeds the inside diameter of the cladding tube 36, the tissue fragment 32 was then able to be withdrawn together with the electrode instrument 10 through axial proximal displacement of the electrode instrument 10 into the cladding tube 36.

Figure 6:
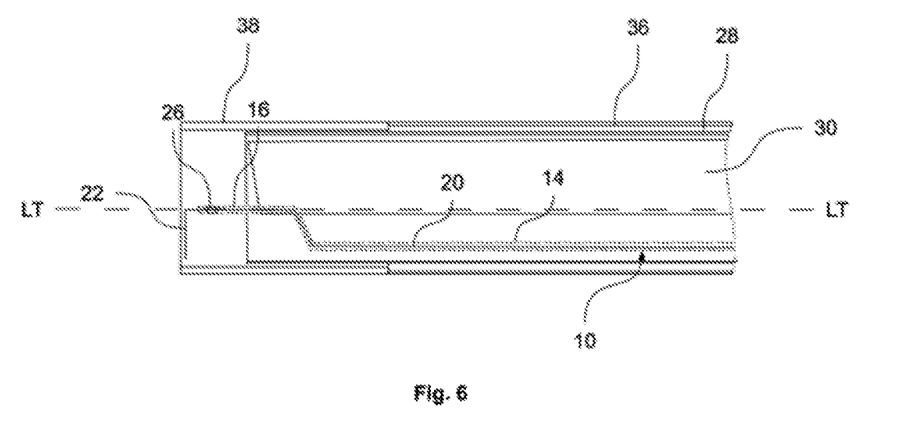
FIG. 6 shows a schematic sectional side view of the distal end region of an alternative resectoscope according to the invention.
Figure 7:
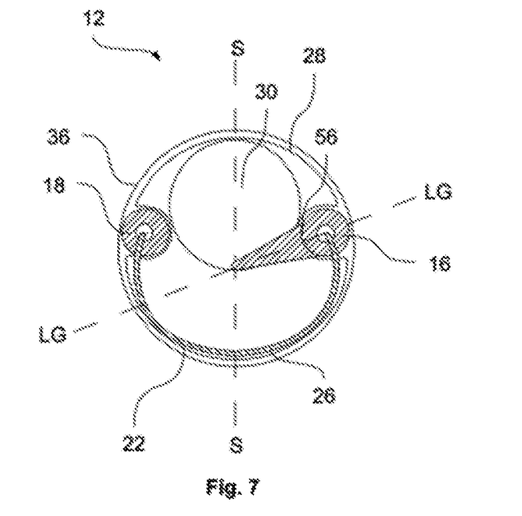
FIG. 7 shows a schematic frontal view of the end region shown in FIG. 6.
Figure 8:
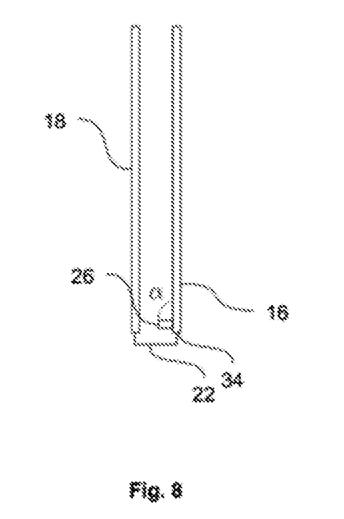
FIG. 8 shows a schematic top view of the electrode instrument that is used in the resectoscope of FIG. 6.
Figure 9:
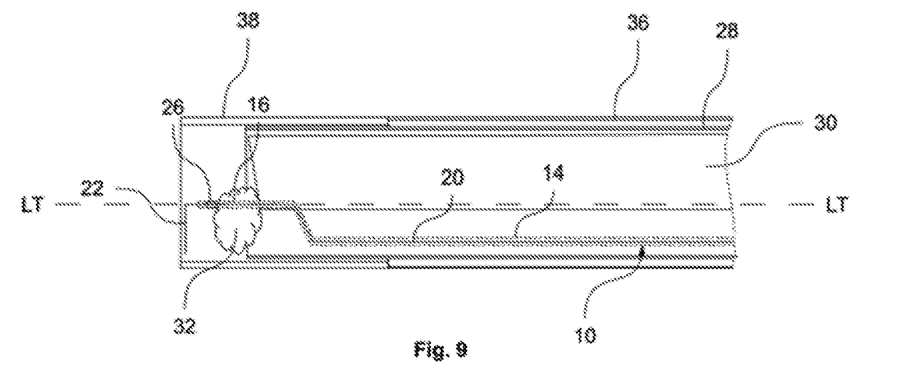
FIG. 9 shows a schematic sectional side view of the end region shown in FIG. 6, a tissue fragment being held between the tissue contact part and optics.
Figure 10:
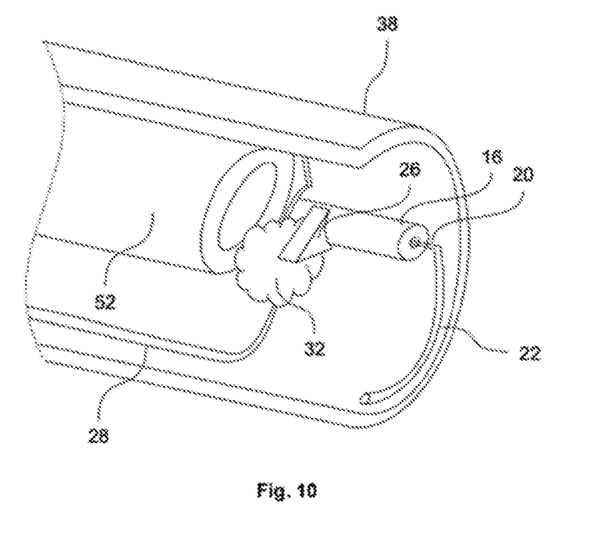
FIG. 10 shows a schematic perspective view of the interior of the end region shown in FIG. 6.

FIG. 6 shows a schematic sectional side view of the distal end region of an alternative resectoscope 12 according to the invention. In contrast to the electrode instrument 10 shown in FIGS. 3 to 5, the electrode instrument 10 shown here has a tissue contact part 26 that is primarily intended for holding tissue fragments 32 between the tissue contact part 26 and an additional component of the resectoscope 12—i.e., not necessarily for the purpose of piercing into a tissue fragment 32, although that is not excluded. FIGS. 6 to 10 show a schematic of the same embodiment, but with the size relationships between the resectoscope components being varied for better visibility. FIG. 7 shows a schematic front view of the end region shown in FIG. 6, while FIG. 8 shows a schematic top view of the electrode instrument used in the resectoscope of FIG. 6. FIG. 9 shows a schematic sectional side view of the end region shown in FIG. 6, a tissue fragment 32 being held between the tissue contact part 26 and optics 52. FIG. 10 shows a schematic perspective view of the interior of the end region shown in FIG. 6.

In the embodiment of FIGS. 6 to 10, the tissue contact part 26 extends from the support arm 16 in the form of a beak or triangle in the direction of the center point of the cladding tube 36. The end of the tissue contact part 26 reaches the sagittal plane S between the support arms, which is the median plane between the two arms. There is no direct connection to the second support arm 18. The connecting surface 56 of the tissue contact part 26 directly adjacent to the outer wall of the insulating sleeve of the support arm 16 has a concave shape that can nestle against the round surface of the support arm 16. This connecting surface 56 borders on the support arm over 20° or more, preferably 35° or more, of its circumference. Alternatively, the tissue contact part 26 can have a tubular portion that encloses the support arm 16 in a form-fitting manner. An especially secure connection between the tissue contact part 26 and the support arm 16 is thus ensured.

The top view of the electrode instrument 10 shown in FIG. 8 shows that the support arms 16 and 18 extend substantially parallel to one another up to the proximal end of the electrode instrument 10. Both support arms 16, 18 have a conductor 20, as can be seen in FIG. 6, in which figure the insulating sleeve 34 is shown in dashed lines. The conductor 20 passes through both support arms 16, 18 and forms an electrode 22 at the distal end of the support arms 16, 18. Here, too, the tissue contact part 26 forms an angle α of approximately 90° with the support arm 16. In other embodiments, it is contemplated that the tissue contact part 26 be curved—to proximal, for example.

Although the present invention has been described in detail with reference to the exemplary embodiments, it is obvious to those skilled in the art that the invention is not restricted to these exemplary embodiments, but rather that modifications can be made in such a way that individual features are omitted or other combinations of the individual features presented are realized, provided that the scope of protection of the appended claims is not exceeded. The present disclosure includes any and all combinations of the individual features presented.

| List of Reference Symbols | |
| --- | --- |
| 10 | electrode instrument |
| 12 | resectoscope |
| 14 | shaft portion |
| 16 | support arm |
| 18 | support arm |
| 20 | conductor |
| 22 | electrode |
| 24 | distal end region |
| 26 | tissue contact part |
| 28 | inner tube |
| 30 | pass-through instrument |
| 32 | tissue fragment |
| 34 | insulating sleeve |
| 36 | cladding tube |
| 38 | insulating tip |
| 40 | holding element |
| 42 | handle |
| 44 | handle part |
| 46 | handle part |
| 48 | spring bridge |
| 50 | carriage |
| 52 | optics |
| 54 | shaft |
| 56 | connecting surface |
| LT | longitudinal axis support arm |
| LG | longitudinal axis tissue contact part |
| α | angle LT/LG |
| S | sagittal plane |

The invention claimed is:

1. An electrode instrument for use in a resectoscope, the electrode instrument having an elongate shaft portion with two support arms through which a conductor extends that forms an electrode at a distal end of the electrode instrument that can be subjected to high-frequency current and is arranged between distal ends of the support arms wherein only one of the support arms has, at a distal end region, a tissue contact part for holding tissue fragments that is arranged on an outer wall of the one of the support arms that has the tissue contact part and is angled in relation to a longitudinal axis of the one of the support arms, the electrode being positioned closer to the distal end than the tissue contact part, wherein: the tissue contact part is configured to hold tissue fragments between the tissue contact part and one of a distal end of an inner tube and a distal end of a pass-through instrument of the resectoscope, a longitudinal axis of the tissue contact part forms an angle of 120° to 60° relative to the longitudinal axis of the one of the support arms, the tissue contact part is composed of an electrically insulating material, and starting from the one of the support arms, the tissue contact part extends from the one of the support arms in a partially circular shape.

2. The electrode instrument as set forth in claim 1, wherein the tissue contact part is arranged in a portion of the one of the support arms that is encased by an electrically insulating sleeve.

3. The electrode instrument as set forth in claim 1, wherein, starting from the one of the support arms, the tissue contact part extends at least into a sagittal plane of the electrode instrument that extends from the one of the support arms to ⅛ of a distance to a second support arm.

4. The electrode instrument as set forth in claim 1, wherein the tissue contact part is designed and arranged so as to pierce into tissue fragments.

5. A resectoscope for endoscopic surgery with a cladding tube, wherein an electrode instrument as set forth in claim 1 is supported in a longitudinally displaceable manner within the cladding tube.

6. The resectoscope as set forth in claim 5, wherein the tissue contact part is arranged at least in some portions distally from an inner tube that is arranged in the cladding tube and/or from a pass-through instrument that is arranged in the cladding tube.

7. The resectoscope as set forth in claim 5, wherein the tissue contact part is arranged proximally from the electrode at least in portions.

8. The resectoscope as set forth in claim 1, wherein the electrode is attached to the distal end of the one of the support arms and does not contact the tissue contacting part.

9. The resectoscope as set forth in claim 1, wherein the tissue contacting part includes a triangular portion that has an angled surface.

10. The resectoscope as set forth in claim 1, wherein the pass-through instrument is a lens.

11. The resectoscope as set forth in claim 1, wherein the tissue contact part includes a curved surface and an entirety of the curved surface directly contacts the one of the support arms.

* * * * *